US012122783B2

(12) United States Patent
Moser et al.

(10) Patent No.: US 12,122,783 B2
(45) Date of Patent: Oct. 22, 2024

(54) STABLE SALT OF 5,10-METHYLENE-(6R)-TETRAHYDROFOLIC ACID

(71) Applicant: MERCK & CIE, Schaffhausen (CH)

(72) Inventors: Rudolf Moser, Schaffhausen (CH); Viola Groehn, Dachsen (CH); Thomas Egger, Wangi (CH); Thomas Ammann, Marthalen (CH)

(73) Assignee: MERCK & CIE, Schaffhausen (CH)

( * ) Notice: Subject to any disclaimer, the term of this patent is extended or adjusted under 35 U.S.C. 154(b) by 195 days.

(21) Appl. No.: 17/496,939

(22) Filed: Oct. 8, 2021

(65) Prior Publication Data

US 2022/0024940 A1    Jan. 27, 2022

Related U.S. Application Data

(63) Continuation of application No. 16/212,056, filed on Dec. 6, 2018, now abandoned, which is a continuation of application No. 14/912,328, filed as application No. PCT/EP2014/067447 on Aug. 14, 2014, now abandoned.

(30) Foreign Application Priority Data

Aug. 14, 2013 (EP) .................... 13004050

(51) Int. Cl.
| *C07D 475/04* | (2006.01) |
| *A61K 31/519* | (2006.01) |
| *A61P 35/00* | (2006.01) |
| *C07D 487/14* | (2006.01) |

(52) U.S. Cl.
CPC ......... *C07D 487/14* (2013.01); *C07D 475/04* (2013.01)

(58) Field of Classification Search
CPC ...... C07D 475/04; A61K 31/519; A61P 35/00
See application file for complete search history.

(56) References Cited

U.S. PATENT DOCUMENTS

| 2,300,505 A | 11/1942 | Hubbard |
| 5,300,505 A | 4/1994 | Muller et al. |
| 5,455,236 A | 10/1995 | Muller et al. |
| 7,196,195 B2 | 3/2007 | Fischer et al. |
| 8,329,912 B2 | 12/2012 | Cleary et al. |
| 9,180,128 B2 | 11/2015 | Moser et al. |
| 2007/0099866 A1 | 5/2007 | Moser et al. |
| 2009/0221594 A1 | 9/2009 | Chen et al. |
| 2010/0179095 A1 | 7/2010 | Mueller et al. |
| 2016/0030573 A1 | 2/2016 | Moser et al. |

FOREIGN PATENT DOCUMENTS

| CN | 1842337 A | 10/2006 |
| EP | 0537492 B1 | 5/1995 |
| JP | 5294968 A | 11/1993 |
| JP | 7018084 A | 1/1995 |
| JP | 2004514675 A | 5/2004 |
| JP | 2005524655 A | 8/2005 |
| JP | 2009514776 A | 4/2009 |
| JP | 2009518305 A | 5/2009 |
| JP | 2010513378 A | 4/2010 |
| RU | 2343923 C2 | 1/2009 |
| WO | 04112761 A2 | 12/2004 |
| WO | 07064968 A2 | 6/2007 |
| WO | 2013059735 A1 | 4/2013 |

OTHER PUBLICATIONS

Office Action in corresponding Japanese Patent Application 2021-183793 mailed Nov. 9, 2022 (pp. 1-10).
Search Report in corresponding RU application 202091271 dated Oct. 8, 2020 (pp. 1-3).
Search Report/ Office Action dated Nov. 28, 2018 issued in corresponding JP application 2016-533926 (pp. (1-3).
Stahly, P., Journal of Pharmacuetical Science, 2006, vol. 66, No. 6, and p. 435-439.
Bastin, R. J., ORG. PROC. RES. & DEV., Jul. 19, 2000, V4 N5, P427-435 {abstract).
Nermuth ed. The Practice of Medicinal Chemistry, Technomics p. 347-365 (1999).
International Search Report dated Sep. 26, 2014 issued in corresponding PCT/EP2014/067447 application pp. 1-3).
Office Action in corresponding JP appln: 2020-083208 dated Sep. 15, 2021 (pp. 1-3).

*Primary Examiner* — Bruck Kifle
(74) *Attorney, Agent, or Firm* — MILLEN, WHITE, ZELANO & BRANIGAN, P.C.; Csaba Henter

(57) ABSTRACT

The present invention is directed towards the hemisulfate salt of 5,10-methylene-(6R)-tetrahydrofolic acid, preferably in substantially crystalline form, as well as pharmaceutical compositions and uses thereof in therapy, preferably chemotherapy.

16 Claims, 7 Drawing Sheets

STABLE SALT OF 5,10-METHYLENE-(6R)-TETRAHYDROFOLIC ACID

FIELD OF TECHNOLOGY

The present invention is directed towards the hemisulfate salt of 5,10-methylene-(6R)-tetrahydrofolic acid, preferably in substantially crystalline form, as well as pharmaceutical compositions and uses thereof in therapy, preferably chemotherapy.

BACKGROUND OF THE INVENTION

The reduced folate 5,10-methylene-5,6,7,8-tetrahydrofolate (5,10-$CH_2$-THF) is known for its efficacy as a cytostatic agent and has been preferably administered in combination with fluorinated pyrimidines, such as 5-fluorouracil (5-FU), in the treatment of solid tumors (Seley, K. L. IDrugs 4 (1), 99, 2001). 5,10-$CH_2$-THF achieves its chemotherapeutic effect together with the base analogue and 5-FU metabolite 5-FdUMP by inhibiting the enzyme thymidylate synthase (TS). TS catalyses the conversion of deoxyuridylate (dUMP) to deoxythymidylate (dTMP), which is an essential building block for DNA synthesis. Deactivation of TS occurs by formation of a covalent, ternary inhibition complex between TS, the base analogue 5-FdUMP, which is a metabolite of 5-FU, and 5,10-$CH_2$-THF. An enhancement of the cytotoxic effect of 5-FU can be achieved by increasing the intracellular concentration of 5,10-$CH_2$-THF, whereupon the stability of the ternary complex is increased. This causes direct inhibition of DNA synthesis and repair, which ultimately results in cell death and delay of tumor growth.

However, there are undesirable properties associated with 5,10-$CH_2$-THF, which up to date limited its pharmaceutical use. It is well known that to be amenable for pharmaceutical use an active agent (such as 5,10-$CH_2$-THF) needs to fulfill several requirements including (i) high (chemical, isomeric, crystalline) stability of the active agent itself as well as pharmaceutical compositions thereof, such that effective storage over an acceptable period of time can be achieved, without exhibiting a significant change in the active agent's physicochemical characteristics, (ii) high (chemical, isomerical, crystalline) purity of the active agent, (iii) ease of handling and processing of the active agent to allow transfer the active agent into suitable formulations, etc.

5,10-$CH_2$-THF is an addition product of tetrahydrofolic acid (THF) and formaldehyde (see e.g. Poe, M. et al. Biochemistry 18 (24), 5527, 1979; Kallen, R. G. Methods in Enzymology 18B, 705, 1971) and is known for its extremely high sensitivity to oxidation by air as well as instability in neutral and/or acidic environments potentially leading to chemical degradation and/or hydrolysis (see e.g. Odin, E. et al., Cancer Investigation 16 (7), 447, 1998; Osborn, M. J. et al., J. Am. Chem. Soc. 82, 4921, 1960; Hawkes, J., and Villota, R. Food Sci. Nutr. 28, 439, 1989). Attempts to stabilize 5,10-$CH_2$-THF included e.g. (i) rigorous exclusion of atmospheric oxygen by the use of special technical devices for the reconstitution of solid formulations and the injection of 5,10-$CH_2$-THF in an air-free environment (see e.g. Odin, E. et al., Cancer Investigation 16 (7), 447, 1998; U.S. Pat. No. 4,564,054); (ii) addition of a reducing agent such as L(+)-ascorbic acid or salts thereof, reduced gamma-glutathione, beta-mercaptoethanol, thioglycerol, N-acetyl-L-cysteine, etc. as an antioxidant for the highly sensitive 5,10-$CH_2$-THF and for THF in particular; (iii) stabilization by means of cyclodextrin inclusion compounds (see e.g. EP 0 579 996 B1); (iv) addition of citrate while adjusting the pH to a basic value (see e.g. EP 1 641 460 B1); or (v) formation of various salts such as the sulfate salt (see e.g. EP 0 537 492 B1).

Nevertheless, there still remains a great need for stabilized 5,10-$CH_2$-THF compounds which show high (chemical, isomerical and/or crystalline) purity and/or possess high stability both as compounds as well as when formulated into pharmaceutical compositions, yet may be efficiently prepared, purified and isolated and/or are amenable to manipulation (e.g. acceptable solubility in pharmaceutically acceptable solvents, flowability and particle size) and/or formulation with negligible decomposition or change of the physical and chemical characteristics of the compound, preferably formulated at a high molar percentage (in order to minimize the quantity of material which must be formulated and administered to produce a therapeutically effective dose).

Yet, the existence of a stable solid (polymorphic) form of a (known) chemical compound with these suitable properties cannot be foreseen. Neither is it predictable what the nature of such a solid form may be, i.e. whether it is a salt, anhydrous, hydrated or solvated form, let alone the specific conditions under which a specific polymorph may be isolated (e.g. crystallization conditions and variables, such as solvent, temperature, pH, etc). Choice and control of such parameters are crucial for obtaining the desired solid form in high purity, stability and processability. These are important factors, which directly affect properties and performance of the products and their further use. It is impossible to predict which of the many variables (i.e. solution pH, temperature, pressure, time, solution composition, type and concentration of additives) will be the determining factor.

It has now surprisingly been found that transformation of the (6R)-isomer of 5,10-$CH_2$-THF [(6R)-5,10-$CH_2$-THF] to its hemisulfate salt provides excellent stability to the compound as well as to pharmaceutical compositions thereof and thereby overcomes the previously discussed known drawbacks. The advantageous stability characteristics of the (6R)-5,10-$CH_2$-THF hemisulfate salt will allow the effective use of this compound in medicinal applications.

SUMMARY OF THE INVENTION

The present invention is directed in a first aspect to the hemisulfate salt of (6R)-5,10-$CH_2$-THF (hereinafter also called hemisulfate salt of the invention or compound of the invention).

Preferably, the hemisulfate salt of (6R)-5,10-$CH_2$-THF is in chemically and/or isomerically and/or crystalline pure form, more preferably, the hemisulfate salt of (6R)-5,10-$CH_2$-THF is in substantially crystalline form.

In specific embodiments, the hemisulfate salt of (6R)-5,10-$CH_2$-THF is in anhydrous form, thus in a preferred embodiment the hemisulfate salt of (6R)-5,10-$CH_2$-THF is in crystalline anhydrous form.

Preferably, the hemisulfate salt of (6R)-5,10-$CH_2$-THF is in a crystalline form characterized by one or more X-ray pattern peak positions at an angle of diffraction 2theta (2θ) of 4.7°, 17.9°, and 23.3° expressed in 2θ±0.2° 2θ (CuKα radiation).

In specific embodiments the hemisulfate salt of (6R)-5,10-$CH_2$-THF is characterised in that it provides a FT-Raman spectrum containing peaks at wavenumbers (expressed in ±2 $cm^{-1}$) of 1672, 1656, 1603, 1553, 1474, 1301, 637, 624 and 363 $cm^{-1}$.

In a further aspect, the present invention is directed to pharmaceutical compositions comprising a hemisulfate salt of (6R)-5,10-CH$_2$-THF and a pharmaceutically acceptable carrier or diluent, optionally further comprising at least one additional therapeutic agent including but not limited to, bactericides, antibiotics, antivirals, antiseptics, antineoplastics, anticancer compounds such as chemotherapeutic agents, antifungals, and/or anti-inflammatory agents or other bioactive or therapeutic agents that are suitable for human use, in particular anticancer compounds such as chemotherapeutic agents, for example 5-FU and derivatives, and antifolates, e.g. methotrexate, Pemetrexed.

In a further aspect, the present invention is directed to the use of a hemisulfate salt of (6R)-5,10-CH$_2$-THF (or pharmaceutical compositions thereof) in therapy, preferably in cancer chemotherapy.

DETAILED DESCRIPTION

Figure 1:
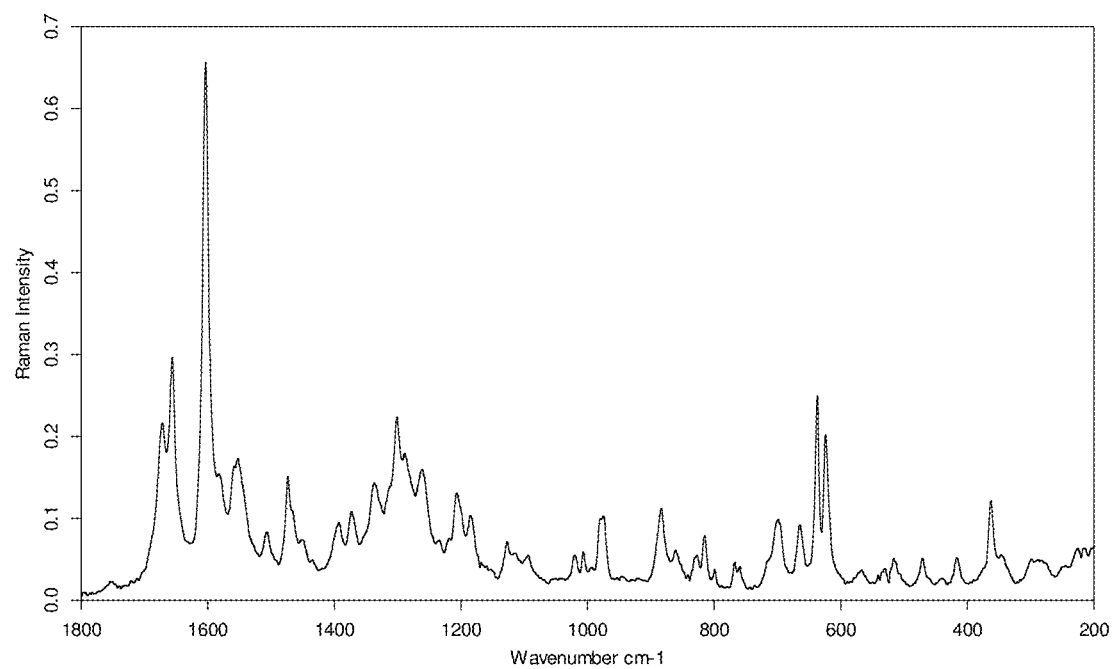
FIG. 1: Raman spectrum of the hemisulfate salt of (6R)-5,10-CH$_2$-THF (Type 1), recorded using a nominal laser power level of 300 mW and 64 scans.

The present invention is directed in a first aspect to a hemisulfate salt of (6R)-5,10-CH$_2$-THF (also referred to as compound of the invention or hemisulfate salt of the invention). In one embodiment the hemisulfate salt of (6R)-5,10-CH$_2$-THF is in substantially crystalline form, more specifically in crystalline anhydrous form.

As used herein, (6R)-5,10-CH$_2$-THF refers to 5,10-CH$_2$-THF in its naturally occurring isomeric form (5,10-methylene-(6R)-tetrahydrofolic acid, N-[4-[(6aR)-3-amino-1,2,5,6,6a,7-hexahydro-1-oxoimidazo[1,5-f]pteridin-8(9H)-yl]benzoyl]-L- glutamic acid), wherein the chiral centers at C6 of the pteridine ring and the α-carbon of the glutamic acid moiety are in their naturally occurring configuration. Thus, the terms "isomeric purity" resp. "stereoisomeric purity", as used herein, refer to the amount of (6R)-5,10-CH$_2$-THF in a sample, which may contain one or more other isomers of the same compound. The terms "isomerically pure" resp. "stereoisomerically pure", as used herein, mean the compound of the invention having an isomeric excess of the desired (6R)-5,10-CH$_2$-THF isomer greater than about 80%, preferably greater than about 90%, preferably greater than about 95%, more preferably greater than about 97%, even more preferably greater than about 99% or more, and most preferably up to 100%, wherein the remainder may be one or more of the other isomers.

The term "crystalline form" (or "polymorph" or "crystal form") as used herein refers to a solid state form which consists of a specific orderly three-dimensional arrangement of structural units. Thus different crystalline forms of the same compound arise from different packing of the molecules in the solid state, which results in different crystal symmetries and/or unit cell parameter. Typically, different solid or crystal forms have one or more different physical and/or chemical property, such as different solubility profiles, different thermodynamic and chemical stabilities, different melting points temperatures and/or different X-ray diffraction patterns, and thus can be distinguished by X-ray diffraction, Infrared (IR) spectroscopy, Differential Scanning calorimetry (DSC), Raman spectroscopy, solid state NMR as well as melting points, density, hardness, optical and electrical properties, stability and/or solubility profile, etc. Little or no regular 3-dimensional arrangement is typically described by the term "amorphous".

The term "crystalline compound" (of the invention) refers to a solid form of the compound of the invention comprising discernable amounts of crystal form(s) or polymorph(s) of the compound of the invention, preferably amounts of greater than 50%, 60%, 70%, 80%, 90% or 95% of one (or more) crystal form(s) or polymorph(s) of the compound of the invention. The amount, degree and nature of the crystallinity of the crystalline compound of the invention may be determined by one or more technical means including optical microscopy, electron microscopy, X-ray powder diffraction, solid state NMR spectroscopy or polarizing microscopy.

As used herein the wording "hemisulfate salt" (of the invention) includes all its specific embodiments and is preferably provided in chemically and/or (stereo)isomerically and/or crystalline pure form. In one specific embodiment it is in substantially crystalline form, more specifically in crystalline anhydrous form (hereinafter also called crystalline form Type 1).

The term "crystalline purity," as used herein, means percentage of a particular crystalline form of a compound in a sample, which may contain the amorphous form of the compound, one or more other crystalline forms of the compound (other than the particular crystalline form of the compound), or a mixture thereof. The term "substantially crystalline form", as used herein, refers to at least about 80%, preferably at least about 90%, preferably at least about 95% crystalline purity, preferably about 97% crystalline purity, more preferably about 99% or more crystalline purity, and most preferably about 100% crystalline purity. Crystalline purity is determined by X-ray powder diffraction (XRPD), Infrared Raman spectroscopy and other solid state methods.

The term "chemical purity," as used herein, means percentage of a particular compound in a sample. The term "substantial chemical purity", as used herein, refers to a compound of the invention in about 80% chemical purity, preferably about 90%, more preferably about 95%, more preferably about 97%, more preferably about 98% chemical purity, and most preferably 99% or higher than 99% or up to 100% chemical purity, as determined by HPLC. Chemical impurities may include unreacted starting material (including solvents), degradation products of (6R)-5,10-CH$_2$-THF (such as THF), etc.

As indicated above, the crystalline form of the hemisulfate salt of the invention (and its purity) may be identified, characterized and distinguished from other salt forms, such as other sulfate salt forms, by unique solid state signatures with respect to, for example, X-ray powder diffraction (XRPD), Infrared Raman spectroscopy and other solid state methods, as shown by the data provided herein.

Thus, in a specific embodiment, the present invention provides a crystalline form of the anhydrous hemisulfate salt of (6R)-5,10-CH$_2$-THF (hereinafter also called crystalline form Type 1), characterised in that it provides:

(i) an X-ray powder diffraction (XRPD) pattern which gives calculated lattice spacings (expressed in 2θ±0.2° 2θ (CuKα radiation)) at 4.7°, 17.9°, and 23.3°, preferably 4.7°, 16.6°, 17.9°, 18.4°, 18.9°, 20.2°, 23.3°, 23.5°, 24.3° and 24.7°; and/or (ii) an FT-Raman spectrum containing peaks at wavenumbers (expressed in ±2 cm$^{-1}$) of 1672, 1656, 1603, 1553, 1474, 1301, 637, 624 and 363 and/or (iii) an IR-spectrum having one or more absorption bands according to Table 3.

In preferred embodiments the hemisulfate salt (Type 1) of the present invention is characterized by at least 2 of the following 10 XRPD peaks (expressed in 2θ±0.2° 2θ (CuKα radiation)) at 4.7°, 16.6°, 17.9°, 18.4°, 18.9°, 20.2°, 23.3°, 23.5°, 24.3° and 24.7°, preferably 4.7°, 17.9°, and 23.3° and at least 2 of the following 9 FT-Raman peaks (expressed in ±2 cm$^{-1}$) of 1672, 1656, 1603, 1553, 1474, 1301, 637, 624 and 363.

In other preferred embodiments, the hemisulfate salt of (6R)-5,10-CH$_2$-THF (Type 1) of the present invention provides an FT-Raman spectrum substantially in accordance with FIG. 1 and/or peaks as reported in Table 1 and/or an X-ray powder diffraction (XRPD) pattern substantially in accordance with FIG. 2(a) and/or peaks as reported in Table 2.

TABLE 1

Raman peak table

| Wavenumber [cm$^{-1}$] | Intensity (qualitative) |
|---|---|
| 3019 | w |
| 2933 | m |
| 2880 | m |
| 1672 | s |
| 1656 | s |
| 1603 | vs |
| 1553 | m |
| 1474 | m |
| 1373 | m |
| 1337 | m |
| 1301 | s |
| 1207 | m |
| 1127 | w |
| 975 | m |
| 884 | m |
| 815 | w |
| 700 | w |
| 665 | w |
| 637 | s |
| 624 | s |
| 363 | m |

(vs = very strong, s = strong, m = medium, w = weak, vw = very weak intensity).

TABLE 2

Powder X-ray diffraction peak table expressed in 2θ ± 0.2° 2θ (CuKα radiation)

| Angle in 2 θ ° | d-spacings in Å | Intensity (qualitative) |
|---|---|---|
| 4.7 | 18.8 | vs |
| 9.4 | 9.4 | vw |
| 11.6 | 7.6 | w |
| 11.8 | 7.5 | w |
| 12.5 | 7.1 | vw |
| 13.6 | 6.5 | vw |
| 14.2 | 6.2 | m |
| 16.6 | 5.35 | s |
| 16.8 | 5.28 | m |
| 17.9 | 4.96 | vs |
| 18.4 | 4.83 | s |
| 18.9 | 4.68 | s |
| 20.2 | 4.38 | s |
| 21.0 | 4.23 | w |
| 21.7 | 4.09 | w |
| 23.3 | 3.82 | vs |
| 23.5 | 3.78 | s |
| 24.0 | 3.70 | m |
| 24.3 | 3.66 | s |
| 24.7 | 3.60 | m |
| 25.1 | 3.54 | m |
| 26.2 | 3.40 | m |
| 26.5 | 3.36 | m |
| 27.0 | 3.30 | m |
| 28.0 | 3.18 | w |
| 29.2 | 3.05 | m |
| 30.4 | 2.94 | w |
| 31.0 | 2.88 | w |
| 31.7 | 2.82 | w |
| 35.5 | 2.53 | w |

(vs = very strong, s = strong, m = medium, w = weak, vw = very weak intensity).

TABLE 3

IR-spectrum of the hemisulfate salt of (6R)-5,10-CH$_2$-THF (Type 1) with absorption bands in cm$^{-1}$ and their assignment

| Absorption band (cm$^{-1}$) | Assignment |
|---|---|
| 3346 | OH and NH stretch |
| 3168 | OH of intramolecular hydrogen bridges, CH$_2$ stretch |
| 1709, 1654 | CO-stretching vibration of monosubstituted amide |
| 1612 | Symmetrical and antisymmetrical stretching vibration of COO$^-$ |
| 1560, 1504 | Aryl and pyrimidine ring stretch |
| 1397, 1300 | Symmetrical and antisymmetrical stretching vibration of COO$^-$ |
| 824 | Aryl adjacent hydrogen wag of para substituted aromatic |

The compound of this invention is most efficiently characterized and distinguished from related compounds by the X-ray powder diffraction pattern as determined in accordance with procedures, which are known in the art (see e.g. J. Haleblian, J. Pharm. Sci. 64:1269, 1975; J. Haleblain and W. McCrone, J. Pharm. Sci. 58:911, 1969). FIG. 2(d), which shows an X-ray diffraction pattern of a hemisulfate salt of (6R)-5,10-CH$_2$-THF as prepared in the Examples in comparison with an X-ray diffraction pattern of the sulfate salt of (6R)-5,10-CH$_2$-THF, illustrates clearly the distinctive pattern of these two salts.

While it is known that the relative intensities of the peaks may vary, depending upon the sample preparation technique, the sample mounting procedure and the particular instrument employed, the compound of the invention can be identified by distinct peaks and peak locations characteristic for the specific polymorph (with a minor variation in peak assignments of about ±0.5 degrees 2theta (2θ), preferably ±0.2 degrees 2theta (2θ) (CuKα radiation).

The compounds of the invention are in unsolvated anhydrous form, which includes compounds that are fully free of water and compounds which may contain traces of water. Such possible residual (not stoichiometric) water content may be any amount of water, but typically ranges from 0 wt.-% $H_2O$ to 3 wt.-% $H_2O$, preferably between 0 wt.-% $H_2O$ and 1 wt.-% $H_2O$.

The hemisulfate compound of the invention can be stored in solid form, such as in form of a powder, lyophilisate, or as a liquid.

In a specific embodiment the compounds of the invention are prepared by adding an aqueous formaldehyde solution of (6S)-THF to an aqueous solution of sulfuric acid (or an aqueous solution of acetic acid and sulfuric acid) and allowing crystallization of the hemisulfate salt of (6R)-5,10-$CH_2$-THF to occur. This crystallization reaction is performed at elevated temperatures, e.g. at a temperature of more than 35° C. In particular, the methods of preparation of the crystalline hemisulfate salt of (6R)-5,10-$CH_2$-THF comprise the steps of (i) reacting a solution of (6S)-tetrahydrofolic acid with an aqueous formaldehyde solution to obtain (6R)-5,10-$CH_2$-THF in solution (according to known procedures), (ii) adding the obtained (6R)-5,10-$CH_2$-THF in solution into an aqueous solution of sulfuric acid (or alternatively into an aqueous solution of acetic acid and sulfuric acid) at a temperature of more than 35° C., preferably between 35° C. and 70° C., more preferably between 40° C. and 60° C., most preferably 40° C. and 50° C. to allow crystallization of the hemisulfate of (6R)-5,10-$CH_2$-THF to occur, and (iii) isolating the obtained crystalline hemisulfate salt of (6R)-5,10-$CH_2$-THF by e.g. filtration.

Step (i) may be carried out according to known procedures as described in the Examples.

In step (ii) the obtained clear solution may be added to a sulfuric acid solution (or an aqueous solution of acetic acid and sulfuric acid) at a temperature of about 40 to 50° C., allowing the selective crystallization of the desired product. Optionally, after addition is completed, the obtained reaction mixture may be stirred at a temperature of about 40 to 50° C., for up to 5 hours, subsequently the crystallized product is then filtered off or centrifuged at the same temperature, optionally washed with water, and dried.

In a further aspect the present invention is directed towards a pharmaceutical composition comprising (a therapeutically effective amount of) the hemisulfate salt of (6R)-5,10-$CH_2$-THF according to the present invention and a pharmaceutically acceptable carrier (also called pharmaceutical composition of the invention) for administration to a patient. The term "pharmaceutically acceptable" as used herein indicates that the carrier is approved or recognized for use in animals, and more particularly in humans, i.e. it is not toxic to the host or patient. In addition a carrier of choice will not interfere with the effectiveness of the biological activity of the active ingredient. The term "carrier" refers to any auxiliary material necessary for the particular mode of administration of choice and includes e.g. solvents (diluents) excipients, or other additives with which the compound of the invention is administered. Typically used diluents pharmaceutical carriers include sterile liquids, such as aqueous solutions and oils (e.g. of petroleum, animal, vegetable or synthetic origin), e.g. peanut oil, soybean oil, mineral oil, sesame oil and the like. Typically used aqueous liquids include water, saline solutions, aqueous dextrose and glycerol solutions and the like. Suitable pharmaceutical excipients include citric acid, ascorbic acid, starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like. Optionally the composition may comprise additives, such as wetting or emulsifying agents, pH buffering agents or binders. Examples of suitable pharmaceutical carriers are well known in the art and are described in e.g. "Remington's Pharmaceutical Sciences" by E. W. Martin (18th ed., Mack Publishing Co., Easton, PA (1990).

Optionally, a pharmaceutical composition of the invention may further comprise at least one additional therapeutic agent. In specific embodiments the at least one additional therapeutic agent may be selected from bactericides, antibiotics, antivirals, antiseptics, antineoplastics, anticancer compounds such as chemotherapeutic agents, antifungals, and/or anti-inflammatory agents or other bioactive or therapeutic agents that are suitable for human use, in particular anticancer compounds such as chemotherapeutic agents. An anticancer drug such as a chemotherapeutic agent, may include but is not limited to chemotherapeutic agents that comprise specific binding members, proteins, nucleic acids or nucleic acid analogs (such as, but not limited to antisense molecules, ribozymes, and siRNAs), lipids, steroids, large molecules, small molecules, or metals. The one or more anticancer drugs can comprise one or more chemotherapeutic agents, such as but not limited to: nucleic acids, in particular fluorinated nucleic acids (e.g. 5-flurouracil or an analog or prodrug thereof), antifolates (e.g. pemetrexed, raltitrexed, lometrexol), topoisomerase inhibitors (e.g. irinotecan, topotecan), antimetabolite drugs (e.g. methotrexate, gemcitabine, tezacitabine), 5-FU modulators, alkylating agents (e.g. cyclophosphamide, carmustine), nucleic acid biosynthesis inhibitors (such as mitomycin, anthracyclines (e.g. epirubicin, doxorubicin), platinum derivatives (e.g. cisplatin, oxaliplatin, carboplatin), microtubule disrupting drugs (e.g. paclitaxel, docetaxel, vinolrebine, vincristine), hormone blocking drugs (e.g. tamoxifen), inhibitors of kinases, including but not limited to receptor and nonreceptor tyrosine kinases (e.g. Iressa, Tarceva, SU5416, PTK787, Gleevec), proteosome inhibitors (e.g. bortezomib), immune modulators (e.g. levamisole), anti-inflammatory drugs, vascularization inhibitors, cytokines (e.g. interleukins, tumor necrosis factors), and drugs that inhibit the activity of cytokines, hormones, or receptors for cytokines or hormones (e.g. the anti-VEGF antibody bevacizumab or "Avastin"). Anticancer drugs may also include monoclonal antibodies, such as but not limited to monoclonal antibodies that bind cytokines, hormones, or hormone receptors (e.g. antibodies that block activation of EGF or VEGF growth factors, such as Avastin, Erbitux, herceptin), etc.

The compounds of the invention or pharmaceutical compositions thereof may be used for therapy, specifically in cancer chemotherapy, i.e. in a method for treatment of cancer, which comprises administering a therapeutically effective amount of a hemisulfate salt of the invention or pharmaceutical compositions thereof to a subject in need of such treatment.

Thus in a further aspect, the present invention is further directed to the use of a hemisulfate salt of the invention (or pharmaceutical compositions thereof) in therapy, preferably in chemotherapy, i.e. in the treatment of cancer. Examples of cancers to be treated according to the invention include, but are not limited to, breast cancer, esophageal cancer, gastric cancer, gall bladder cancer, bile duct cancer, colon cancer, rectal cancer, liver cancer, pancreatic cancer, ovarian cancer, head and neck cancer, and mesotheolioma cancer.

A suitable pharmaceutical composition of the invention may be adapted for oral, parenteral or rectal administration and, as such, may be in the form of tablets, capsules, oral liquid preparations, powders, lyophilisates, granules, lozenges, reconstitutable powders, injectable or infusable solutions or suspensions or suppositories. Preferably, the pharmaceutical compositions are in a form suitable for parenteral administration, such as intravenously or intramuscularly, subcutaneously, intra-arterially.

For parenteral administration, fluid unit dosage forms typically comprise a compound of the invention, optionally a further therapeutic agent, and a pharmaceutically acceptable carrier or diluent, to form e.g. water-based solutions or oil-based suspensions (or lyophilisates thereof). The compound, depending on the presence of other therapeutic agents, the carrier, and concentration used, may be either suspended or dissolved in a carrier. For parenteral solutions, the compound may be dissolved for injection and filter sterilised before filling into a suitable vial or ampoule and sealing. Optionally, adjuvants such as a local an aesthetic, preservatives and buffering agents are dissolved in the vehicle. If desired, the obtained solutions may be subjected to lyophilization (i.e. the composition may be frozen after filling into the vial and the water removed under vacuum). For parenteral suspensions, the compound is suspended in the vehicle (instead of being dissolved) and preferred sterilization includes exposure to ethylene oxide before suspension in a sterile vehicle (such as a vial or ampoule). Optionally, a surfactant or wetting agent may be included in the composition to facilitate uniform distribution of the compound.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

In case of a combination therapy wherein a pharmaceutical composition of the invention comprises a compound of the invention and at least one further therapeutic agent, the active agents may be administered as part of the same pharmaceutical composition or the at least one further therapeutic agent may be administered separately, i.e. as a separate (and possibly different) pharmaceutical compositions, optionally via different administration routes, either simultaneously or sequentially.

The dose of the active agent(s), i.e. the compound of the invention (and optionally the at least one further therapeutic agent), used in a treatment as described herein, will depend on various factors, including age and health condition of the subject to be treated, type and severity of the disease to be treated, route and frequency of administration, and the like. Those skilled in the art of cancer treatment and chemotherapy would be able to determine therapeutically effective amounts and regimens for the compound of the invention alone or in combination with at least one further therapeutic agent as defined above, based on known protocols for evaluating toxicity and efficacy.

The term "therapeutically effective amount" refers to the amount of active compound that elicits the biological or medicinal response in a tissue, system, animal, individual or human that is being sought by a skilled practitioner (e.g. researcher, veterinarian, medical doctor or other clinician or caregiver), which includes (i) prevention of the disease; and/or (ii) inhibition of the disease (e.g. arresting further development of the pathology and/or symptomatology); and/or (iii) amelioration of the disease (e.g. reversing the pathology and/or symptomatology). Likewise the term "treatment" as used herein refers to (i) prevention of the disease; and/or (ii) inhibition of the disease (e.g. arresting further development of the pathology and/or symptomatology); and/or (iii) amelioration of the disease (e.g. reversing the pathology and/or symptomatology).

A pharmaceutical composition of choice may contain from 0.1% to 99 wt %, preferably from 10 to 60 wt %, of the active agent (i.e. the compound of the invention optionally in combination with at least one further therapeutic agent), depending on the method of administration.

Typical dosage ranges of the compound of the invention to be used in cancer treatment may range from 10 mg/m$^2$ to 1 g/m$^2$, preferably from 50 mg/m$^2$ to 500 mg/m$^2$ (for colorectal cancer treatment) resp. 10 mg/m$^2$ to 200 mg/m$^2$ (for Methotrexate therapy), and more preferably from about 100 mg/m$^2$ to about 250 mg/m$^2$ (for colorectal cancer treatment) resp. 50 mg/m$^2$ to 150 mg/m$^2$ (for Methotrexate therapy).

The following Examples serve as illustration of the present invention without intending to limit its scope.

EXAMPLES

Differential Scanning Calorimetry (Thermal Analysis Q2000): Closed (hermetically sealed) gold crucibles; sample filled under ambient conditions or after 3 minutes of equilibration in an N$_2$ environment; heating rate of 10 K min-1; −50° C. to 254° C. range. When two heating scans were carried out, the sample was rapidly cooled to −50° C. between the scans. Listed transition temperatures correspond to peak maxima and minima, not to onset temperatures.

FT-Raman Spectroscopy (Bruker RFS100; with OPUS 6.5 software; offline data analysis carried out with OPUS 7.0 software): Nd:YAG 1064-nm excitation; 300 mW nominal laser power; Ge detector; 64-256 scans; 3500-100 cm$^{-1}$ spectral range used for analysis; 2 cm$^{-1}$ resolution.

$^1$H-NMR (Bruker DPX300): $^1$H-NMR spectra were recorded using a proton frequency of 300.13 MHz, a 30° excitation pulse, and a recycle delay of 1 s. Either 16 or 256 scans were accumulated, and deuterated DMSO was used as the solvent. The solvent peak was used for referencing, and chemical shifts are reported on the TMS scale.

$^{13}$C NMR (Bruker AMX 300): The $^{13}$C NMR spectrum was obtained using a Bruker AMX 300 spectrometer equipped with a 5 mm TXO probehead. The hemisulfate was dissolved in 0.1N NaOD. The spectrum was measured at 303 K, with 4000 scans and a digital resolution of 32768 data points. Chemical shifts are given in ppm relative to internal TSP (((3-trimethylsilyl)-2,2',3,3'-tetradeuteropropionic acid, sodium salt)) standard.

Powder X-Ray Diffraction (Bruker D8 Advance): Copper Kα radiation, 40 kV/40 mA, LynxEye detector, Bragg-Brentano reflection geometry, 0.02° 2θ step size, 37 s step time, 2.5-50° 2θ range. Powder samples were measured in 0.1-mm or 0.5-mm deep silicon single-crystal sample holders. No special treatment was used in preparing the samples other than the application of slight pressure to get a flat surface. An ambient air atmosphere was used for all measurements, and the samples were rotated during the measurement. Absent any information to the contrary X-Ray Diffraction data is shown as reflection data.

Powder X-Ray Diffraction (Stoe Stadi P.): Copper Kα1 radiation, 40 kV/40 mA, Mythen1K detector, transmission mode, curved Ge monochromator, 0.02° 2θ step size, 60 s step time, 1.5-50.5° 2θ scanning range with 1° 2θ detector step in step-scan mode. The samples (10-20 mg of powder) were measured between two acetate foils. No special treatment was used in preparing the samples. An ambient air atmosphere was used for all measurements, and each sample was rotated during the measurement.

TG-FTIR (Netzsch Thermo-Microbalance TG 209 with Bruker FT-IR Spectrometer IFS 28): Al crucible (with microhole); $N_2$ atmosphere; 10 K $min^{-1}$ heating rate; 25° C. to 300° C. range.

IR (FT-IR Paragon 1000): The infrared spectrum was recorded in 100 scans on a Perkin Elmer Fourier Transform Infrared System from a hemisulfate sample pressed in a bromide disk.

Example 1: Preparation of (6R)-5,10-$CH_2$-THF Hemisulfate Salt

A solution of (6S)-tetrahydrofolic acid (16 mmol, 7.93 g) in 78.0 g distilled water was provided in a roundbottom flask at room temperature under $N_2$. The pH of this solution was adjusted to pH 11 by adding (slowly) a 32% NaOH solution. As soon as the solution became clear, a 1.00M HCl solution was added to adjust the pH of the solution to 8.3 at 25° C. The obtained clear solution was cooled to about 0° C., at which temperature it showed a pH of 8.8. By addition of 1M HCl the pH was adjusted to pH=8.6 and 1.44 g of a 36.8% HCHO solution (110 mol %) were added in one portion. Upon completion of the addition the solution was stirred at 0° C. (ice bath) for 1 hour. Active charcoal (0.2 g, Norit C Extra) was added and the reaction mixture was stirred for 30 minutes at 0° C. and then cold filtered over a suction filter to obtain a clear solution, which was used in step (b) without further purification.

(b) A mixture of 55 ml 1M $H_2SO_4$ (0.055 mol; 344 mol %) was provided in a roundbottom flask at 60° C. under $N_2$. To this solution was added dropwise over a time period of 15 minutes the solution as obtained in step (a) and the obtained reaction mixture was stirred at 50° C. for 2 hours. The reaction mixture was then filtered at 50° C. over a suction filter, washed twice with 25 ml distilled water at room temperature and dried at 30° C. and 10 mbar for 12 hours (overnight) to obtain the (6R)-5,10-$CH_2$-THF hemisulfate salt in form of light gray crystals (7.36 g, 86% yield). The obtained product had a purity of 98.4% as determined by HPLC, an isomeric purity of 97.6% (6R-isomer). Analysis by XRPD showed the crystal form Type 1 (for complete characterization see Examples 2 and 3).

Figure 2:
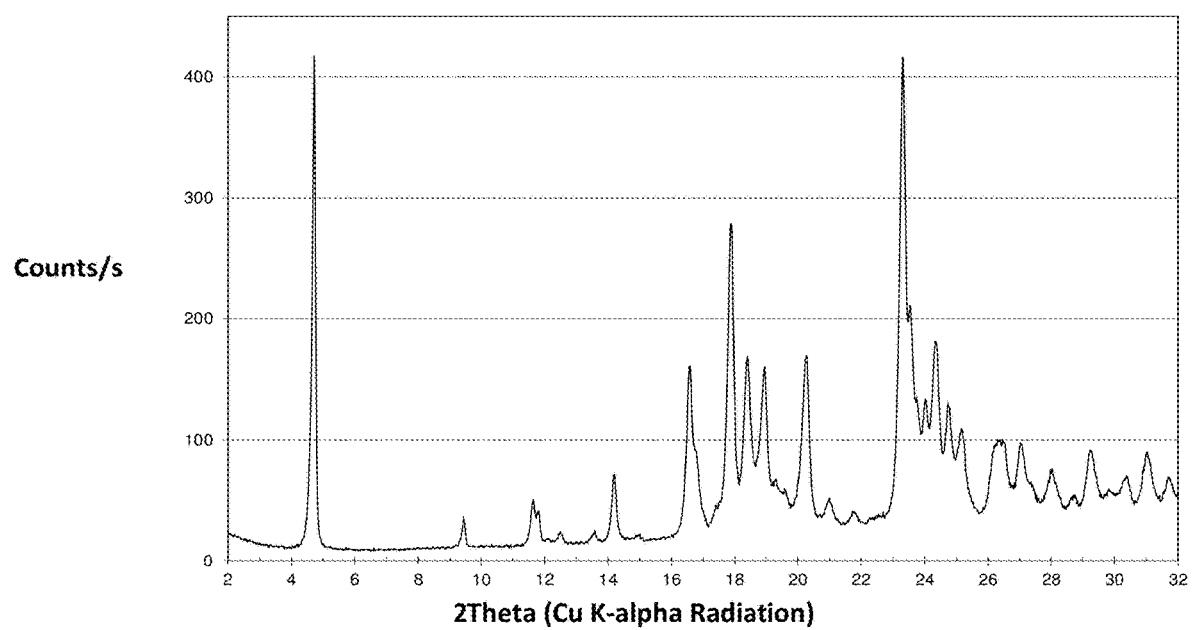
FIG. 2(a): X-Ray Powder Diffractogram of the hemisulfate salt of (6R)-5,10-CH$_2$-THF (Type 1) recorded in the reflection mode; 2(b): X-Ray Powder Diffractogram of the hemisulfate salt of (6R)-5,10-CH$_2$-THF (Type 1) recorded in the transmission mode; 2(c): Comparison of X-ray diffraction pattern of the hemisulfate salt of (6R)-5,10-CH$_2$-THF (Type 1) recorded in transmission mode (upper curve A) with a recording of the same compound recorded in reflection mode (lower curve B); 2(d): Comparison of X-ray diffraction pattern of the hemisulfate salt of (6R)-5,10-CH$_2$-THF (Type 1) (upper curve A) with an X-ray diffraction pattern of the sulfate salt of (6R)-5,10-CH$_2$-THF (lower curve B) recorded in the transmission mode.
Figure 2:
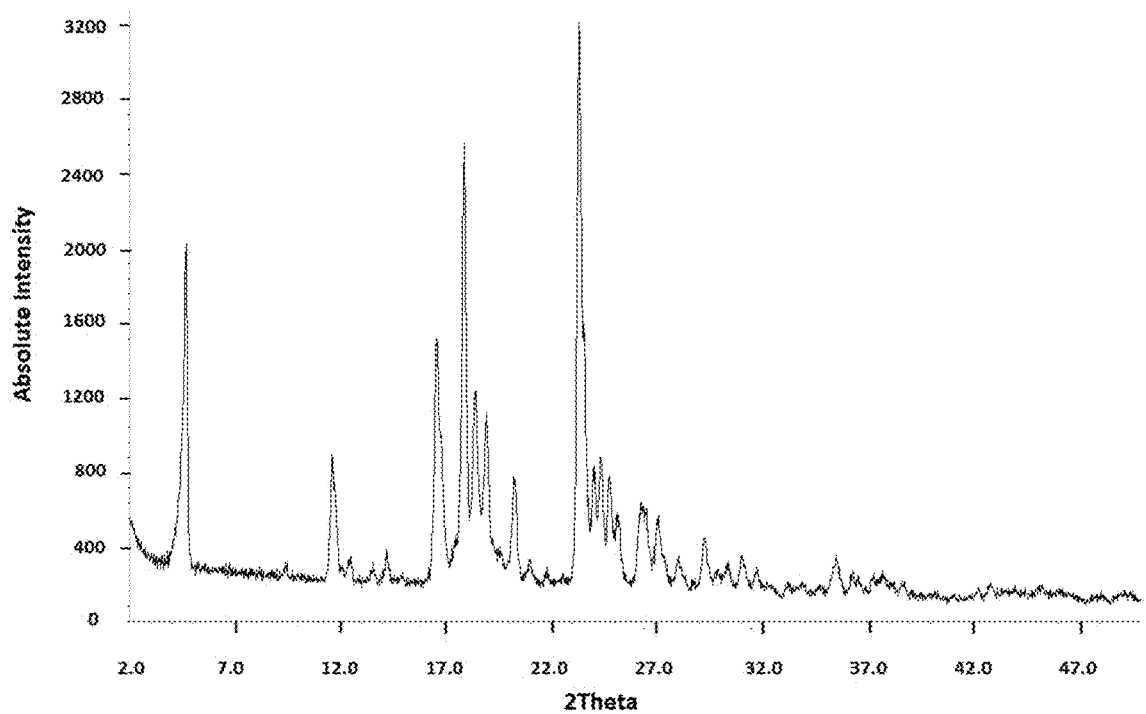
Figure 2:
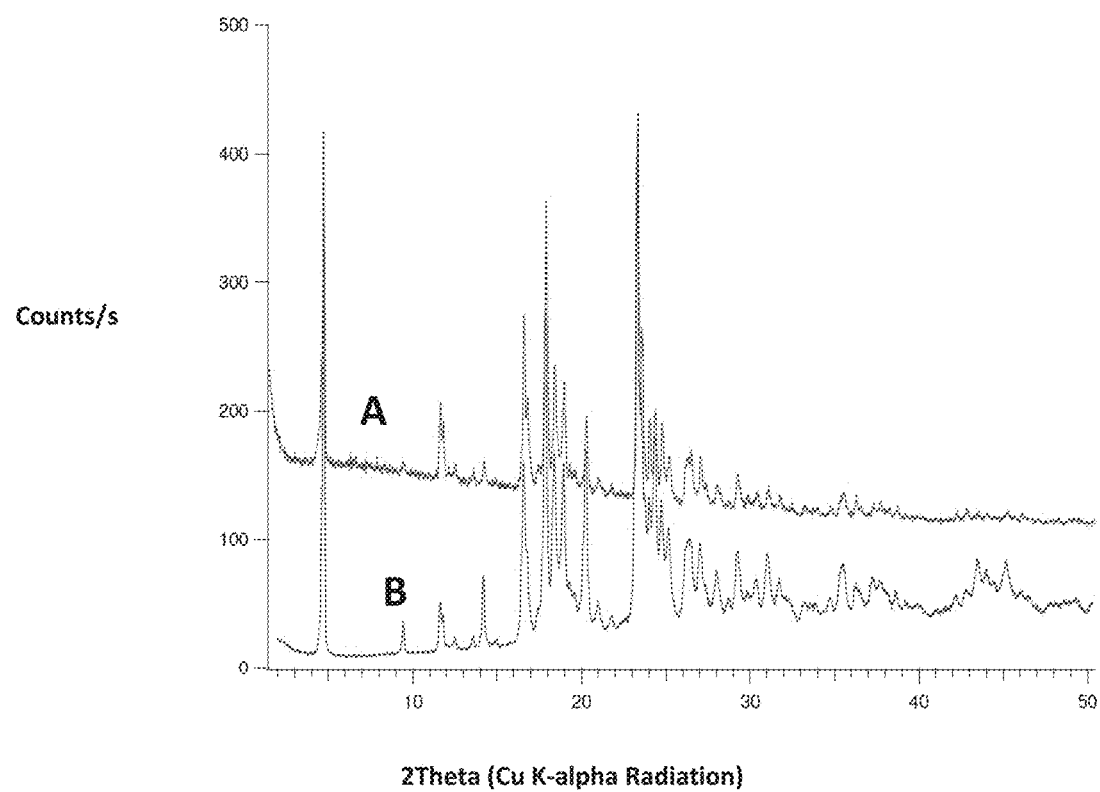
Figure 2:
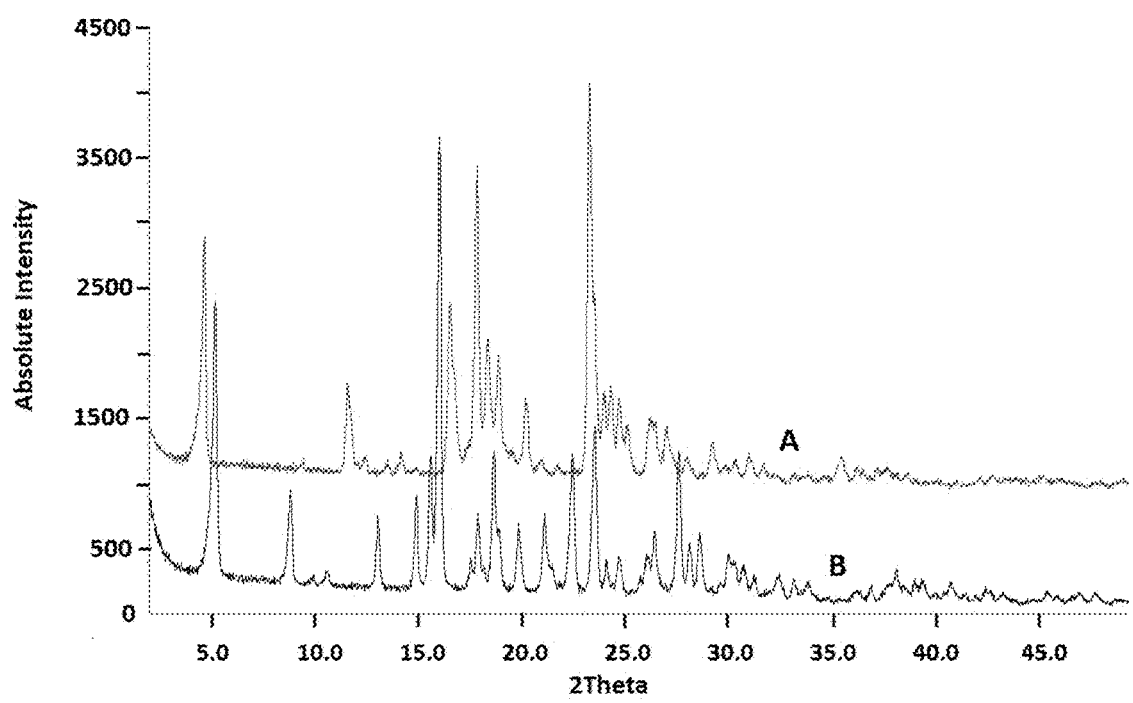
Figure 3:
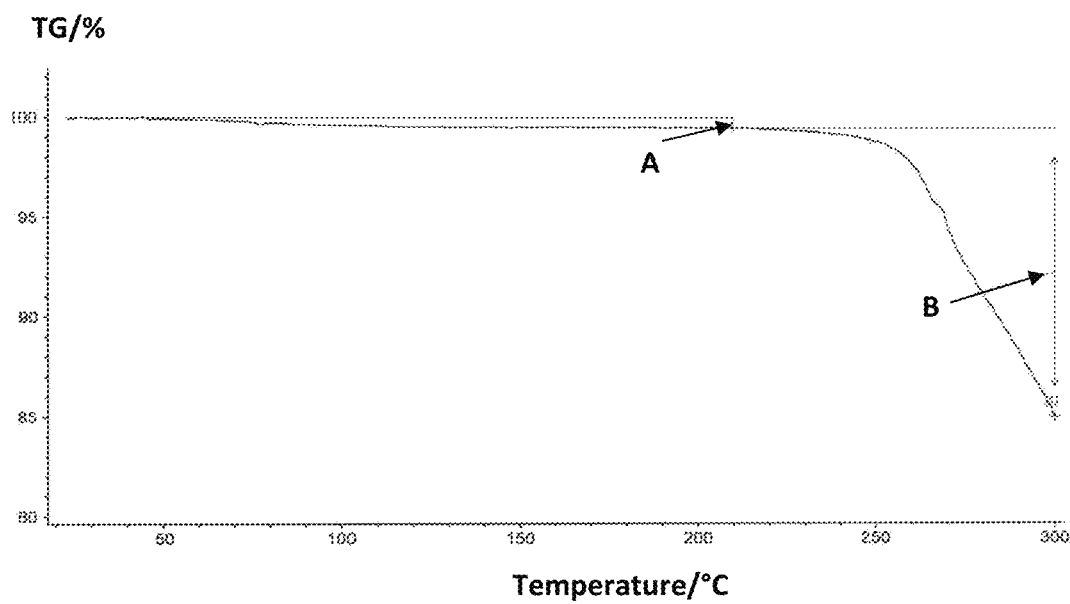
FIG. 3: TG-FTIR thermogram of the hemisulfate salt of (6R)-5,10-CH$_2$-THF (Type 1). "A" indicates a change in mass of −0.5% (due to loss of water) and "B" indicates a change in mass of −14.53% (due to decomposition)
Figure 4:
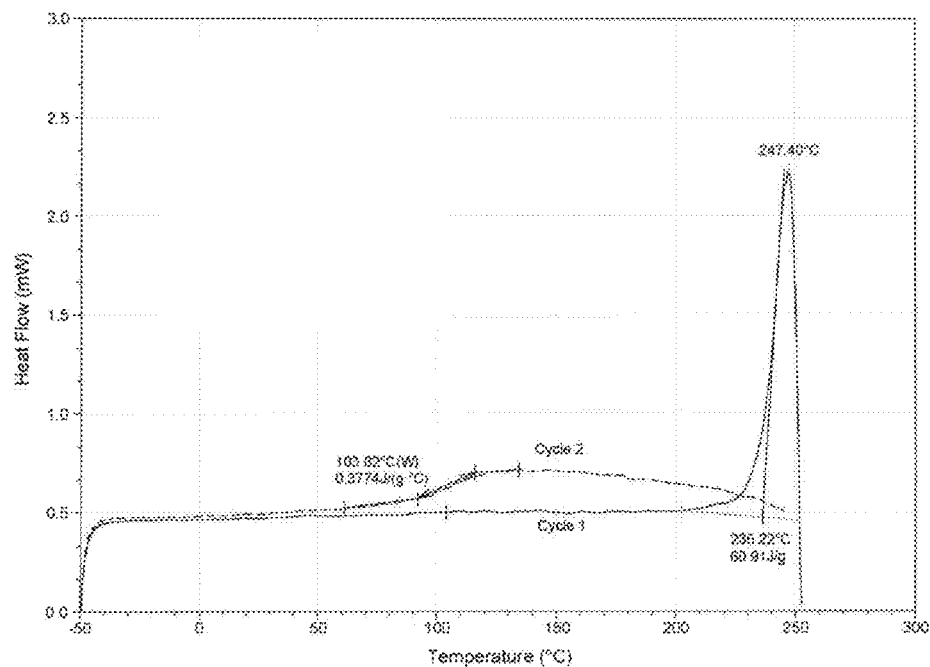
FIG. 4: DSC thermogram of the hemisulfate salt of (6R)-5,10-CH$_2$-THF (Type 1; first scan: solid line; second scan (after quench cooling): dashed line).

Example 2: Characterization (a) The FT Raman spectrum of (6R)-5,10-$CH_2$-THF hemisulfate salt, recorded using a nominal laser power level of 300 mW and 64 scans is shown in FIG. 1.
(b) The corresponding powder X-ray diffractogram, recorded in transmission mode, is shown in FIG. 2.
(c) The TG-FTIR thermogram of (6R)-5,10-$CH_2$-THF hemisulfate salt is shown in FIG. 3. It was carried out under $N_2$ flow (to avoid oxidative degradation). The sample shows a loss of 0.5 wt % $H_2O$ from ca. 40° C. to 210° C., which is residual water (due to either hygroscopicity or incomplete drying). Decomposition occurs only above 210° C.
(d) The DSC thermogram of (6R)-5,10-$CH_2$-THF hemisulfate salt is shown in FIG. 4. Prior to the first heating scan, the sample was equilibrated for three minutes under gaseous nitrogen flow and lost 0.6 wt.-% of its mass during that time. This is consistent with the water content observed in the TG-FTIR thermogram (see FIG. 3) and confirms that this water is loosely bound. The sample was subsequently heated in a closed gold crucible to 254° C. at 10 K $min^{-1}$, quench cooled to −50° C., and heated a second time at 10 K $min^{-1}$. The only thermal event in the first heating scan is an endothermal at approximately 247.4° C. ($\Delta H \approx 60.9$ J $g^{-1}$), which is attributable to melting. This endothermal event possibly overlaps with the onset of an exothermic degradation. In the second heating scan, a glass transition is observable at Tg≈104° C. ($\Delta Cp=0.38$ J $g^{-1}K^{-1}$), which confirms that melting occurred in the first scan. No other thermal events were observed up to 250° C.
(e) The IR spectrum was recorded in a pressed KBr pellet and the characteristic absorption bands are shown in Table 3.
(f) The $^1$H NMR spectrum of (6R)-5,10-$CH_2$-THF hemisulfate salt was recorded in DMSO-$d_6$ and the chemical shifts (d) in ppm are shown in Table 8.

TABLE 8

$^1$H-NMR of the hemisulfate salt of (6R)-5,10-$CH_2$-THF with chemical shifts (d) in ppm

| δ (1H) | Multiplicity | Intensity |
|---|---|---|
| 7.75 | d | 2H |
| 6.62 | d | 2H |
| 4.99 | m | 1H |
| 4.33 | m | 1H |
| 3.74 | m | 2H |
| 3.52 | m | 1H |
| 3.28 | m | 2H |
| 2.91 | m | 1H |
| 2.33 | t | 2H |
| 2.17 | m | 1H |
| 2.05 | m | 1H |

(d = doublet, m = multiplet, t = triplet; with TSP at 0 ppm and solvent D2O/NaOD 4.85 ppm)

(g) The $^{13}$C NMR was recorded in 0.1N NaOD and the chemical shifts (d) in ppm relative to TSP are shown in Table 9.

TABLE 9

$^{13}$C-NMR of the hemisulfate salt of (6R)-5,10-$CH_2$-THF with chemical shifts (d) in ppm

| δ (13C) | Multiplicity | δ (13C) | Multiplicity |
|---|---|---|---|
| 185.12 | s | 114.19 | d |
| 182.05 | s | 103.99 | s |
| 173.12 | s | 70.67 | t |
| 172.41 | s | 58.61 | d |
| 162.26 | s | 56.94 | d |
| 156.78 | s | 51.6 | t |
| 151.78 | s | 41.71 | t |
| 131.18 | d | 37.07 | t |
| 123.27 | s | 31.41 | t |

(d = doublet, m = multiplet, t = triplet)

(h) Analysis of (6R)-5,10-$CH_2$-THF hemisulfate salt by optical microscopy confirmed its crystallinity. The sample consisted of agglomerates of small, birefringent particles.

Example 3: Stability Testing of (6R)-5,10-$CH_2$-THF Hemisulfate Salt (a) Suspension equilibration of (6R)-5,10-$CH_2$-THF hemisulfate salt as starting material at temperatures other than room temperature in a variety of solvents and mixture are summarized in Table 10:

TABLE 10

Suspension equilibration stability of (6R)-5,10-CH$_2$-THF hemisulfate salt

| Solvent(s) | Temperature (° C.) | Duration (h: hours; d: days) | Observation |
|---|---|---|---|
| MeOH/formic acid 1:1 | 50 | 2 h | No change |
| AcOH saturated with L-ascorbic acid | 50 | 1 d | No change |
| THF with ~2 mM L-ascorbic acid | 40 | 3 d | No change |
| 2-PrOH with ~2 mM L-ascorbic acid | 40 | 3 d | No change |
| PEG4500/EtOH 1:9 saturated with L-ascorbic acid | 50 | 7 d | No change |
| H$_2$O | 5 | 6 d | No change |
| formic acid/THF 1:3 | 10-20 | 6 d | No change |
| AcOH saturated with L-ascorbic acid | 50 | 5 d | No change |
| MeCN saturated with L-ascorbic acid | 50 | 5 d | No change |

(b) Stability in 85% ethanol at room temperature (6R)-5,10-CH$_2$-THF hemisulfate salt (3.01 g) was dispersed in 100 ml 85% EtOH at room temperature and stirred for 5 h, then filtered and dried at 30° C. and 8 mbar for 12 hours (over night). Analysis by XRPD showed that the X-ray pattern distinctive for the crystal form Type 1 remained unchanged.

(c) Stability at high temperature/low pressure (6R)-5,10-CH$_2$-THF hemisulfate salt (2.17 g) was placed in a drying chamber at 65° C. and 8 mbar for 21 h. Analysis by XRPD showed that the X-ray pattern distinctive for the crystal form Type 1 remained unchanged.

(d) Long-term stability of (6R)-5,10-CH$_2$-THF hemisulfate salt and pharmaceutical composition thereof In order to determine the long-term stabilities of (6R)-5,10-CH$_2$-THF hemisulfate salt, the compounds of the invention were stored in air at 25° C. and at 60% relative humidity. The content of (6R)-5,10-CH$_2$-THF hemisulfate salt remaining was measured by HPLC at periodic intervals and is given by comparison with the initial value (% rel.). The results are shown in Table 11.

TABLE 11

Long-term stability of three different production batches of (6R)-5,10-CH$_2$-THF hemisulfate salt

| | (6R)-5,10-CH$_2$-THF hemisulfate (% rel.) | | | | | | | |
|---|---|---|---|---|---|---|---|---|
| | 0 months | 3 months | 6 months | 9 months | 12 months | 18 months | 24 months | 36 months |
| (6R)-5,10-CH$_2$-THF hemisulfate (batch 1) | 100.0 | 99.7 | 99.5 | 99.6 | 99.2 | 99.2 | 99.4 | 98.5 |
| (6R)-5,10-CH$_2$-THF hemisulfate (batch 2) | 100.0 | 99.9 | 99.9 | 100.0 | 99.7 | 99.4 | 99.4 | 99.0 |
| (6R)-5,10-CH$_2$-THF hemisulfate (batch 3) | 100.0 | 99.5 | 99.5 | 99.4 | 99.1 | 99.0 | 99.0 | |

In order to determine the long-term stabilities of (6R)-5,10-CH$_2$-THF hemisulfate salt as pharmaceutical compositions, more specifically as lyophilisates (as prepared according to e.g. Example 5), lyophilisates were stored in air at 25° C. and at 60% relative humidity. The content of (6R)-5,10-CH$_2$-THF hemisulfate salt remaining was measured by HPLC at periodic intervals and is given by comparison with the initial value (% rel.). The results are shown in Table 12.

TABLE 12

Long-term stability of five different production batches of (6R)-5,10-CH$_2$-THF hemisulfate salt as a lyophyilisate

| | (6R)-5,10-CH$_2$-THF hemisulfate (% rel.) | | | | | | | |
|---|---|---|---|---|---|---|---|---|
| | 0 months | 3 months | 6 months | 9 months | 12 months | 18 months | 24 months | 36 months |
| (6R)-5,10-CH$_2$-THF hemisulfate (batch A) | 100.0 | 100.1 | 100.2 | 99.9 | 100.0 | 99.7 | 100.0 | |
| (6R)-5,10-CH$_2$-THF hemisulfate (batch B) | 100.0 | 100.1 | 99.9 | 100.0 | 99.8 | 99.7 | 100.1 | |
| (6R)-5,10-CH$_2$-THF hemisulfate (batch C) | 100.0 | 99.6 | 99.7 | 99.8 | 99.5 | 99.6 | 99.2 | 98.6 |
| (6R)-5,10-CH$_2$-THF hemisulfate (batch D) | 100.0 | 100.0 | 99.8 | 99.4 | 99.4 | 99.3 | 99.2 | 99.4[1)] |

TABLE 12-continued

Long-term stability of five different production batches of (6R)-5,10-CH$_2$-THF hemisulfate salt as a lyophyilisate

| | (6R)-5,10-CH$_2$-THF hemisulfate (% rel.) | | | | | | |
|---|---|---|---|---|---|---|---|
| | 0 months | 3 months | 6 months | 9 months | 12 months | 18 months | 24 months | 36 months |
| (6R)-5,10-CH$_2$-THF hemisulfate (batch E) | 100.0 | 100.1 | | | 99.7 | | 99.4 | 98.9 |

$^{1)}$Value for 45 months

Table 11 and Table 12 clearly show that (6R)-5,10-CH$_2$-THF hemisulfate is highly stable over a long period of time even at room temperature as a pure compound as well as in form of a pharmaceutical composition such as a lyophilisate.

Example 4: Comparative Stability of (6R)-5,10-CH$_2$-THF Sulfate Salt

In order to compare the long-term stabilities of (6R)-5,10-CH$_2$-THF hemisulfate salt, the compounds of the invention, to the long-term stabilities of (6R)-5,10-CH$_2$-THF sulfate salt prepared according to EP 0 537 492 B1, stability data for (6R)-5,10-CH$_2$-THF sulfate salt has been generated at various temperatures and humidities.

(a) Stability of (6R)-5,10-CH$_2$-THF sulfate (6R)-5,10-CH$_2$-THF sulfate salt was prepared according to literature procedures (EP 0 537 492 B1) and stored for 15 month at −20° C. Subsequently, samples of the product were stored at 5° C. resp. at 25° C. and 60% relative humidity resp. at 40° C. and 75% relative humidity. The content of (6R)-5,10-CH$_2$-THF sulfate salt remaining in the sample was measured by HPLC at periodic intervals. The content of (6R)-5,10-CH$_2$-THF sulfate was compared to the initial value at the time of preparation (% rel.). The results are shown in Tables 13 and 14.

TABLE 13

Long-term stability of (6R)-5,10-CH$_2$-THF sulfate salt at −20° C.

| Temperature/relative humidity | (6R)-5,10-CH$_2$-THF sulfate (% rel.) | |
|---|---|---|
| | 0 months | 15 months |
| −20° C. | 100.0 | 98.7 |

TABLE 14

Subsequent long-term stability of (6R)-5,10-CH$_2$-THF sulfate salt at 5° C., 25° C./60% rh, resp. 40° C./75% rh

| Temperature/relative humidity | (6R)-5,10-CH$_2$-THF sulfate (% rel.) | |
|---|---|---|
| | 0 months | 6 months |
| 5° C. | 98.7 | 97.3 |
| 25° C./60% rh | 98.7 | 95.5 |
| 40° C./75% rh | 98.7 | 95.0 |

A comparison of the data in Tables 13 and 14 with the stability data of (6R)-5,10-CH$_2$-THF hemisulfate as disclosed in Example 3 clearly shows that i) there is a remarkable difference in stability of (6R)-5,10-CH$_2$-THF hemisulfate compared to (6R)-5,10-CH$_2$-THF sulfate and ii) (6R)-5,10-CH$_2$-THF hemisulfate is much more stable over a long period of time than (6R)-5,10-CH$_2$-THF sulfate.

(b) Content of the degradation product 10-formyl-(6R)-tetrahydrofolic acid (6R)-5,10-CH$_2$-THF sulfate salt was prepared according to literature procedures (EP 0 537 492 B1) and stored for 15 month at −20° C. Subsequently, samples of the product were stored at 5° C. resp. at 25° C. and 60% relative humidity resp. at 40° C. and 75% relative humidity. The content of 10-formyltetrahydrofolic acid, a major degradation product, was measured by HPLC at periodic intervals and disclosed as absolute values (% w/w). The results are shown in Tables 15 to 16.

TABLE 15

Content of the degradation product 10-formyltetrahydrofolic acid when stored at −20° C.

| Temperature/relative humidity | 10-formyltetrahydrofolic acid (% w/w) | |
|---|---|---|
| | 0 months | 15 months |
| −20° C. | 0.53 | 1.37 |

TABLE 16

Subsequent content of the degradation product 10-formyltetrahydrofolic acid when stored at 5° C., 25° C./60% rh, resp. 40° C./75% rh

| Temperature/relative humidity | 10-formyltetrahydrofolic acid (% w/w) | |
|---|---|---|
| | 0 months | 6 months |
| 5° C. | 1.37 | 1.47 |
| 25° C./60% rh | 1.37 | 1.89 |
| 40° C./75% rh | 1.37 | 2.36 |

Example 5: Pharmaceutical Dosage Forms of (6R)-5,10-CH$_2$-THF Hemisulfate Salt (a) Lyophilisate for reconstitution to be used for intravenous application To 18.480 kg water at 4° C. where argon was sparged through for 1 hour 1.386 kg NaOH 2M and 968.9 g sodium citrate trihydrate was added. The mixture was stirred at 4° C. under argon up to a complete dissolution (pH 13.0). 473.9 g (6R)-5,10-CH$_2$-THF hemisulfate was then added under using 210 g of argon saturated rinse water of 4° C. (slow dissolution, pH 6.5). The pH was then set with NaOH 2M to 9.3±0.1 (121.8 g). 203.6 g of argon saturated water of 4° C. was added (total solution 21.844 kg).

The solution then was filtered through a sterile filter. Into each vial of 10 ml 5.201 g (5 ml) of the sterile filtrated solution was added and then lyophilized at −45° C.

Before injection 10 ml of water (WFI) was added to each vial (293 mosmol/kg).

(b) Formulation of a lyophilized composition of (6R)-5,10-CH$_2$-THF hemisulfate at an essentially neutral pH The following materials (mg/100 ml) and procedure were used for obtaining the lyophilized composition:

Materials (mg/100 ml):
  5.530 g (6R)-5,10-CH$_2$-THF hemisulfate salt (equivalent to 5.000 g (6R)-5,10-CH$_2$-THF)
  6.000 g Citric acid, Anhydrous, Powder, USP
  4.000 g Ascorbic acid, Granular, USP
  NaOH/HCl to adjust pH
  100 mg Water for Injection (WFI), USP to qs
  (i) Procedure: Sparge WFI with filtered Nitrogen Gas, NF for 30 min.
  (ii) Record tare wt of 100 ml plastic bottle.
  (iii) Weigh out citric acid, ascorbic acid and about 90 g N$_2$ sparged water.
  (iv) Mix to dissolve.
  (v) Adjust pH to 7.0±0.1 with 1N NaOH or HCl.
  (vi) Chill the solution to 10° C.
  (vii) Add (6R)-5,10-CH$_2$-THF hemisulfate salt, mix to dissolve.
  (viii) Record pH (7.0±0.2).
  (ix) Add more water to 110 g final weight (or 100 ml). Record wt.
  (x) Pass through a 0.2-micron filter while keeping the solution chilled as possible.
  (xi) Fill into vials (2 ml or 100 mg 5,10-CH$_2$-THF per vial) while keeping the solution chilled as possible.
  (xii) Freeze dry.
  (xiii) Seal vials under slight vacuum with nitrogen in the headspace.
  (xiv) Crimp the vials.

Example 6: Preclinical/Clinical Results (a) Results from pre-clinical investigations in animal models, performed according to the ICH S9 guidance, show that (6R)-5,10-CH$_2$-THF hemisulfate is safe at the highest dose-levels administered to rats (100 mg/kg/day) and dogs (50 mg/kg/day). Clinical data furthermore show that (6R)-5,10-CH$_2$-THF hemisulfate administered in doses of up to 200 mg/m$^2$ is safe for patients.

(b) In a single-blinded, randomized phase I/II study (ISO-CC-002) performed on 32 patients diagnosed with colon cancer the pharmacokinetic and pharmacodynamic properties of (6R)-5,10-CH$_2$-THF hemisulfate compared to Levoleucovorin in tumor tissue, adjacent mucosa and blood plasma were investigated. The study was performed at the Sahlgrenska University Hospital in Göteborg, Sweden. The analysis of the completed trial data showed that administration of (6R)-5,10-CH$_2$-THF hemisulfate gave substantially greater exposure and peak plasma concentrations of methylenetetrahydrofolate than those obtained after administration of Levoleucovorin. The concentrations of methylenetetrahydrofolate and tetrahydrofolate in both tumor and adjacent mucosa were also much higher after administration of (6R)-5,10-CH$_2$-THF hemisulfate than those obtained after administration of Levoleucovorin.

The invention claimed is:

1. Hemisulfate salt of 5,10-methylene-(6R)-tetrahydrofolic acid.

2. A pharmaceutical composition containing a pharmaceutically acceptable carrier and an effective amount of the hemisulfate salt of 5,10-methylene-(6R)-tetrahydrofolic acid, which is in substantially crystalline form.

3. Hemisulfate salt according to claim 1 having at least 80% chemically and/or isomerically and/or crystalline purity.

4. A combination of the hemisulfate salt according to claim 1 with at least one additional therapeutic agent which is a: bactericide, antibiotic, antiviral, antiseptic, anticancer compound, antifungal, anti-inflammatory agent, or antifolate.

5. Hemisulfate salt according to claim 1 in anhydrous form which is unsolvated and optionally crystalline, and which may contain a small amount of residual water which is not stoichiometric.

6. Hemisulfate salt of 5,10-methylene-(6R)-tetrahydrofolic acid, which is crystalline and has three or more X-ray pattern peak positions at an angle of diffraction 2 theta selected from the group consisting of 4.7°, 16.6°, 17.9°, 18.4°, 18.9°, 20.2°, 23.3°, 23.5°, 24.3° and 24.7° expressed in 2θ±0.2° 2θ (CuKα radiation, reflection), which is sufficient for the recognition of this compound as the crystalline hemisulfate salt of 5,10-methylene-(6R)-tetrahydrofolic acid.

7. Hemisulfate salt according to claim 6, which is provided as a powder.

8. Hemisulfate salt according claim 1 having a FT-Raman spectrum containing one or more peaks at wavenumbers (expressed in ±2 cm$^{-1}$) of 1672, 1656, 1603, 1553, 1474, 1301, 637, 624 and 363, wherein any one of these peaks is sufficient to confirm the identity of the compound as the hemisulfate salt of 5,10-methylene-(6R)-tetrahydrofolic acid.

9. Hemisulfate salt according to claim 1 having a FT-Raman spectrum substantially in accordance with FIG. 1 and/or having an X-ray powder diffraction (XRPD) pattern substantially in accordance with FIG. 2(*a*) or 2(*b*).

10. Hemisulfate salt according to claim 1 having at least 2 of the following 10 XRPD peaks (expressed in 2θ±0.2° 2θ (CuKα radiation)) at 4.7°, 16.6°, 17.9°, 18.4°, 18.9°, 20.2°, 23.3°, 23.5°, 24.3° and 24.7° and at least 2 of the following 9 FT-Raman peaks (expressed in ±2 cm$^{-1}$) of 1672, 1656, 1603, 1553, 1474, 1301, 637, 624 and 363, wherein a combination of at least one of said 10 XRPD peaks and at least one of said 9 FT-Raman peaks amounts to two data points that sufficiently signifies that the compound is the hemisulfate salt of 5,10-methylene-(6R)-tetrahydrofolic acid.

11. Hemisulfate salt according to claim 1 having at least 2 of the following 3 XRPD peaks (expressed in 2θ±0.2° 2θ (CuKα radiation)) at 4.7°, 17.9°, and 23.3° and at least 2 of the following 5 FT-Raman peaks (expressed in ±2 cm$^{-1}$) of 1672, 1656, 1603, 1553, 1474, 1301, 637, 624 and 363, wherein a combination of at least one of said 3 XRPD peaks and at least one of said 5 FT-Raman peaks amounts to two data points that sufficiently signifies that the compound is the hemisulfate salt of 5,10-methylene-(6R)-tetrahydrofolic acid.

12. A pharmaceutical composition comprising a hemisulfate salt of 5,10-methylene-(6R)-tetrahydrofolic acid according to claim 1 and a pharmaceutically acceptable carrier, which carrier may be injectable water.

13. The pharmaceutical composition according to claim 12 in the form of tablets, capsules, oral liquid preparations, powders, lyophilisates, granules, lozenges, reconstitutable powders, injectable or infusable solutions or suspensions or suppositories.

14. The pharmaceutical composition according to claim 12 further comprising at least one additional therapeutic agent.

15. The pharmaceutical composition according to claim 12, which is a pharmaceutical composition for oral, parenteral or rectal administration.

16. A method for providing substantially greater exposure and peak plasma concentrations of methylenetetrahydrofolate than those obtained after administration of Levoleucovorin, comprising administering a hemisulfate salt of 5,10-methylene-(6R)-tetrahydrofolic acid in accord with claim 1.

* * * * *